United States Patent [19]

Gernes

[11] 4,086,653
[45] Apr. 25, 1978

[54] PNEUMATIC PUMP MONITOR

[75] Inventor: David B. Gernes, Watertown, Mass.

[73] Assignee: Thermo Electron Corporation, Waltham, Mass.

[21] Appl. No.: 647,841

[22] Filed: Jan. 9, 1976

[51] Int. Cl.² .............................................. G01F 1/00
[52] U.S. Cl. ........................................ 364/564; 3/1.7; 73/223; 364/571
[58] Field of Search .................... 235/151.3; 128/1 D; 3/1.7; 73/223

[56] References Cited

U.S. PATENT DOCUMENTS

| | | | |
|---|---|---|---|
| 3,550,162 | 12/1970 | Huffman et al. | 128/1 D |
| 3,718,044 | 2/1973 | Joyce et al. | 3/1.7 |
| 3,783,453 | 1/1974 | Bolie | 3/1.7 |

Primary Examiner—Eugene G. Botz
Attorney, Agent, or Firm—James L. Neal; David W. Gomes

[57] ABSTRACT

A monitor for a pneumatically driven blood pump receives an input correlated to mechanical operation of the blood pump and electrically transforms the information to clinical information related to such factors as stroke volume of the pump, average stroke volume, flow rate and beat rate.

10 Claims, 4 Drawing Figures

PNEUMATIC PUMP MONITOR

The invention described herein was made in the course of or under a contract with the U.S. Department of Health, Education and Welfare.

SUMMARY OF THE INVENTION

A monitor is provided for a pneumatically driven blood pump. The blood pump includes a flexible bladder enclosed in a rigid housing. Gas rhythmically injected and released between the bladder and the housing repetitively collapses the bladder to produce pumping action in cooperation with one-way valves located at outlet and inlet conduits to the pump. A fixed quantity of compressible gas is isolated in the space defined between the bladder and the housing, thereby forming a closed pneumatic system.

During operation, pressure and volume information related to the closed pneumatic system is fed to the pump monitor and processed electrically to provide such clinical information as stroke volume of the pump on a beat per beat basis, the average stroke volume, flow rate and beat rate of the pump.

The volume derived information from the closed pneumatic system is processed to compensate for compressibility of the gas according to the Perfect Gas Law $P_1V_1/T_1 = P_2V_2/T_2$. Because the relevant temperatures are not readily determined, the Perfect Gas Law is taken in its adiabatic form $P_1V_1 = P_2V_2$ even though the system is not adiabatic. A correction factor is introduced which, nonetheless, causes the system to provide accurate representations of the clinical information.

DETAILED DESCRIPTION OF THE DRAWINGS

Figures 1, 2:
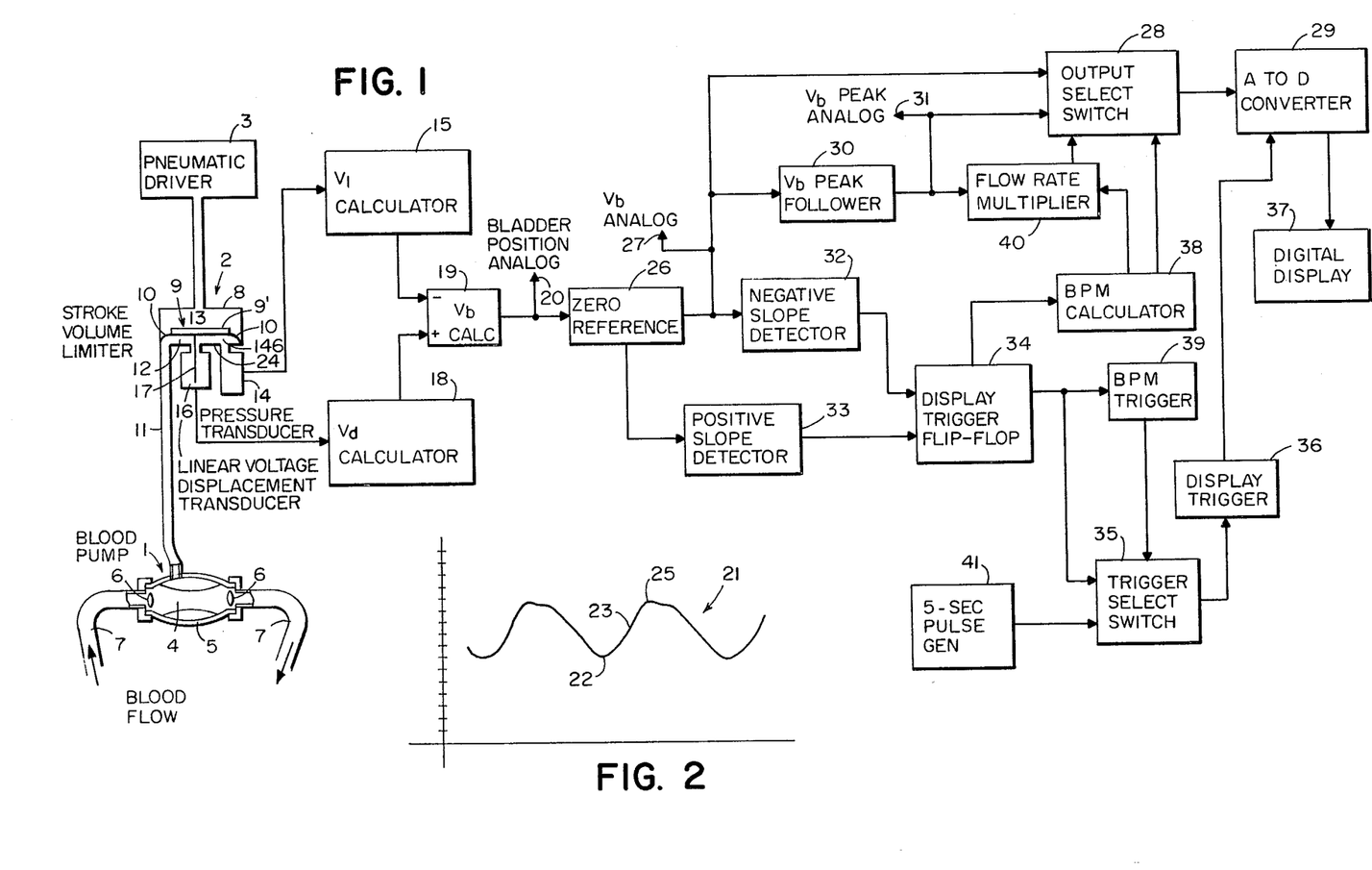
FIG. 1 is a schematic representation illustrating a preferred embodiment of the pneumatic pump monitor of this invention.
FIG. 2 is a sample bladder position analog signal obtainable from the monitor of FIG. 1.

With reference to FIG. 1, a pneumatic blood pump system includes a blood pump 1, a device 2 for limiting the stroke volume of the pump 1 and a pneumatic driver 3. The blood pump 1 comprises a flexible bladder 4 enclosed by a rigid housing 5. A rhythmical injection of gas between the bladder 4 and the housing 5 repeatedly collapses the bladder to produce pumping action in cooperation with one-way valves 6 located at inlet and outlet conduits 7. One example of such a blood pump is disclosed in U.S. patent application Ser. No. 647,842, filed Jan. 9,1976, for "Pneumatic Blood Pump" in the name of Victor L. Poirier.

The stroke volume limiter 2 controls the amount of gas injected into the blood pump 1 and is described in detail in U.S. patent application Ser. No. 647,679, filed Jan. 9, 1976, for "Blood Pump Pneumatic Control" in the name of Victor L. Poirier. Briefly, the limiter 2 comprises a chamber 8 enclosing a diaphragm 9. A circumferential portion 10 of the diaphragm 9 creates a seal between a centrally rigid portion 9 of the diaphragm 9 and the chamber 8. This isolates a fixed quantity of air in a closed pneumatic system 146 defined by the space between the bladder 4 and housing 5 of the blood pump 1, a pneumatic drive line 11, and a volume 12 in the chamber 8. Compressed gas is rhythmically injected and released by the pneumatic driver 3 into the chamber volume 13. This cycles the diaphragm 9 and causes the gas confined between the diaphragm 9 and the bladder 4 to move back and forth alternately collapsing the bladder and allowing it to fill. The diaphragm 9 moves between fixed stops to control the amount of gas injected into the pump, thus to control stroke volume of the pump.

The volume of gas, air in the preferred embodiment, in the closed pneumatic system 146, is used in calculating operating parameters of the pump 1. At the chamber end, the diaphragm 9 displaces and compresses a known volume, $V_d$, of gas in the closed system. As a result, the bladder 4 in the pump 1 collapses. Reduction in the bladder volume is the stroke volume, $V_b$.

Prior to diaphragm movement, the bladder 4 fills from the left ventricle of the heart; pressure can be as low as 10 m.m.Hg. At the point of maximum diaphragm displacement the bladder pumps at greater than arterial pressure, typically approximating 100 m.m.Hg. At the pumping pressure substantial compression of the gas between the bladder 4 and the diaphragm 9 occurs, with the attendant loss of volume. According to the present invention, the stroke volume, $V_b$, of the pump 1 is calculated by subtracting the loss of volume due to compression, $V_1$, from the known displacement volume, $V_d$, defined by the area of the diaphragm 9 and the length of its stroke.

As to the block diagram shown in FIG. 1, the blocks represent functions performed by parts of the structure. The lines connecting the blocks refer mainly to signals and not the precise wiring in the circuit.

In FIG. 1, Pressure Transducer 14 constantly reads the pressure of the closed system 146 and outputs the reading in electrical form to the $V_1$ Calculator 15. Using this information, the $V_1$ Calculator 15 computes the volume lost from the closed system 146 due to the compression of the gas. Simultaneously, the Linear Voltage Displacement Transducer 16 feeds information on the position of the displacement of the diaphragm 9, in electrical form, to the $V_d$ Calculator 18. The calculator 18 computes the amount of compressive displacement, $V_d$, being introduced into the closed system 146.

The two signals representing lost volume, $V_1$, and compressive displacement, $V_d$, are inputed to the $V_b$ Calculator 19. This calculator 19 subtracts $V_1$ from $V_d$ continuously to arrive at an analog wave representing the position of the bladder 4. One possible output is a sinusoidally shaped wave 21 of FIG. 2, each complete oscillation representing a complete cycle of the pump 1. This wave is the Bladder Position Analog signal 20 of FIG. 1. Important information contained by this wave is represented by the positioning of the high and low peaks and the peak to peak height. For example, the peak to peak height of the wave 21 is directly proportional to the stroke volume, $V_b$. The Bladder Position Analog signal 20 is fed to the Zero Reference circuit 26 to set the voltage of the low peak equal to zero volts. Thus, the voltage level of the high peak is directly proportional to the stroke volume, $V_b$. The output of the circuit 26 is the $V_b$ Analog signal 27. For the immediate extraction of a value for stroke volume, $V_b$, the signal 27 is connected to the Output Select Switch 28. The switch 28 is manually operated and connects the selected one of four analog inputs to the Analog to Digital Converter 29 (hereinafter A to D Converter 29). In the $V_b$ Analog Position, the $V_b$ Analog signal 27 is so connected. The converter 29 extracts the stroke volume information by being signaled to read the voltage at its input at the precise moment of each individual high peak of the signal 27. The signal to the converter for sampling comes from the Display Trigger 36 and its associated circuitry, to be subsequently described. The value of the stroke volume, extracted from the blood pump system parameters, is outputed in visual digital form by the Visual Digital Display 37. In the embodiment of the present invention herein described, the A to D Converter 29 and the Visual Digital Display 37 are incorporated into a single device referred to as a Digital Panel Meter, Model No. AD 2002 DP supplied by Analog Devices Inc. of Westwood, Massachusetts.

Additionally, the stroke volume information from the $V_b$ Analog signal 27 is stored in analog form by the $V_b$ Peak Follower 30. The output of the follower 30 is an analog signal representing the high peak value of the $V_b$ Analog signal 27. This output, the $V_b$ Peak Analog signal 31, is fed to the Output Select Switch 28. Like the stroke volume, the information of this signal 31 can be outputed to the Visual Digital Display 37, with proper positioning of the switch 28 and a proper triggering signal, to be described subsequently, being given to the A to D Converter 29.

Another connection of the $V_b$ Analog signal 27 is to the Negative Slope Detector 32. The slope of the $V_b$ Analog signal 27 being positive immediately prior to the high peak, the Negative Slope Detector 32 produces a signal in digital form representing the beginning of the negative slope of the $V_b$ Analog signal 27. This digital signal accurately determines the position of the high peak of the signal 27. This digital signal is fed into the Display Trigger Flip-Flop 34 and there induces a logical "set" operation. The Flip-Flop 34 serves as a logic memory device with two stable states. The "set" operation signifies a change of the output from a logical "0" to a logical "1".

Simultaneously with the connection to the Negative Slope Detector 32, the $V_b$ Analog signal 27 is also fed to the Positive Slope Detector 33. This slope detector 33 generates a digital signal identifying the beginning of a positive slope on the $V_b$ Analog signal 27. This digital signal induces the logical "reset" operation of the Display Trigger Flip-Flop 34.

The resulting output of the Display Trigger Flip-Flop 34 is a rectangular pulse wave which changes from a logical "0" to a logical "1" on occurrence of a high peak in $V_b$ Analog signal 27. This particular change of state of the Display Trigger Flip-Flop 34 is used to determine the time at which the A to D Converter 29 samples the $V_b$ Analog signal 27. To accomplish this, the Trigger Select Switch 35 is ganged with the Output Selector Switch 28. When the $V_b$ Analog signal 27 is chosen at the output switch 28, the Trigger Select Switch 35, driven by the same mechanical selection, connects the output of the Flip-Flop 34 to the Display Trigger 36. This trigger 36 responds to the "set" operation of the Display Trigger Flip-Flop 34 by signaling the A to D Converter 29 to sample its analog input. The result is that the A to D Converter samples the $V_b$ Analog signal 27 at a point close enough to the high peak to insure accuracy in the reading.

The "set" action of the Display Trigger Flip-Flop 34 is also a measure of the beats per minute of the blood pump. The measurement is made by the BPM Calculator 38. The calculator 38 transforms the digital signals from the Flip-Flop 34 into an analog signal directly proportional to the beat rate of the blood pump. This analog signal is available for selection by the Output Select Switch 28.

The appropriate sampling signal for output of the beat rate information is derived from the "set" operation of the Flip-Flop 34. The output of the Flip-Flop 34 is connected to the BPM Trigger 39. For proper triggering of the beat rate output, a slight delay is needed after the high peak point of the $V_b$ Analog signal 27. This delay is produced by the BPM Trigger 39, to be discussed with reference to FIG. 3. The output of this trigger 39 is connected to the Trigger Select Switch 35 which continues the connection to the Display Trigger 36 when the Output Select Switch 28 is in the Beat Rate position.

The Beat Rate Analog signal 145 is an input to the Flow Rate Multiplier 40. The multiplier 40 also receives the $V_b$ Peak Analog signal as an input and multiplies the two inputs to compute a value for the flow rate of the blood pump 1. The result in analog form, is available as an output by the proper setting of the Output Select Switch 28. The trigger signal, simultaneously connected to the Display Trigger 36 by the Trigger Select Switch 35, is the same signal used to trigger the $V_b$ Analog signal output. That is, the set operation of the Flip-Flop 34 triggers the Flow Rate signal output.

The remaining trigger signal is for the $V_b$ Peak Analog signal 31 from the $V_b$ Peak Follower 30. When the Output Select Switch 28 selects the $V_b$ Peak Analog output, the Trigger Select Switch 35 connects the 5-Second Pulse Generator 41 to the display trigger 36. This causes the A to D Converter 29 to sample the $V_b$ Peak Analog signal 31 every five seconds.

Returning to the Blood pump system as previously described, the closed system 146 undergoes a known volumetric compressive displacement, $V_d$. This results in a loss of volume, $V_1$, due to compression in the closed system and an expansion of the system, via the bladder 4, equal to the stroke volume, $V_b$. Therefore, the stroke volume, $V_b$, may be defined by the equation $$V_b = V_d - V_1. \tag{1}$$

The volume lost in the closed system 146 due to compression, $V_1$, is defined by the equation $$V_1 = V_0 - V_m, \tag{2}$$

where $V_0$ represents the volume of the closed system when it is not being compressed by the diaphragm 9, and $V_m$ represents the volume of the closed system during compression. $V_0$ is a known constant for any particular blood pump system. In order to compute a value for $V_m$, the equation for the Perfect Gas Law, $$P_o V_o / T_o = P_m V_m / T_m \tag{3}$$

can be used. In equation (3), the subscript "$o$" represents the closed system condition of zero compression, and the subscript "$m$" represents the closed system condition of maximum compression.

Rearranging equation (3) to solve for $V_m$, $$V_m = P_o V_o / P_m \cdot T_m / T_o. \tag{4}$$

At this point, in order to avoid the attendant difficulties of obtaining responsive temperature information on the closed system 146, the temperature changes are treated as minimal and the ratio $T_m/T_o$ is set equal to unity. This and other inaccuracies will be compensated for by a correction factor to be subsequently discussed.

Substituting the resulting form of equation (4) for $V_m$ in equation (2), the equation (2) becomes $$V_1 = V_o - P_o V_o/P_m. \tag{5}$$

Rearranging this equation, $$V_1 = V_o 1 - (P_o/P_m), \tag{6}$$
$$V_1 = V_o (P_m - P_o/P_m). \tag{7}$$

The equation (7) is in the form which is solved by the $V_1$ Calculator 15 of FIG. 1. The terms are defined as follows:

$V_o$ is the known volume of the closed system 146 under zero compression by the diaphragm 9;

$P_o$ is the pressure of the closed system 146 under the same condition; and $P_m$ is the pressure of the closed system 146 under maximum compression.

$P_m$ is derived from the pressure transducer 14 which gives a reading proportional to the difference between the sampled pressure and the pressure to which the transducer is zeroed. If the transducer is zeroed to the zero compression system pressure, $P_o$, the pressure of the closed system 146 may be represented as $$P_m = P_o + P_t, \tag{8}$$

where $P_t$ is the pressure reading of the transducer 14. Substituting equation (8) for $P_m$ in equation (7), $$V_1 = V_o P_t/P_o + P_t. \tag{9}$$

The equation (9) is solved by the circuit of the present invention. In the preferred embodiment of the entire system including the blood pump 1, the stroke volume limiter 2 and the monitor of this invention, the zero compression pressure $P_o$ of the closed system 146, is set equal to atmospheric pressure. Also the pressure transducer 14 is zeroed to atmospheric pressure. These conditions, however, should not be construed to limit the application of the present invention. The pressure transducer 14 used in the embodiment herein described is available from TYCO Instruments, Inc., 4 Hartwell Place, Lexington, Mass. 02173. PN 49084 (15 psi), Model AB.

A correction factor is subtracted from equation (9) in order to compensate for would be inaccuracies, notably that resulting from setting $T_m/T_o$ equal to unity in the derivation of equation (5). The form of the correction factor is the positive rate of change of the volume lost due to compression. This correction factor is used to reduce the signal from which it is derived. Signal reduction occurs only while the value of the solution is positive and increasing the amount of correction is more fully described in connection with FIG. 3.

The only differences between equations (7) and (9) represent particulars of the pressure transducer 14 as used by the herein described circuit. Therefore, although equation (9) is actually solved by the circuit, the equation (7) best represents an important aspect of this invention.

FIG. 2 shows an illustrative response characteristic of the Bladder Position Analog signal 20 and the $V_b$ Analog signal 27, both discussed in connection with FIG. 1. The parameters of blood pump operation vary significantly generating a wide variety of different output shapes for the signal 20.

The high and low peaks act relative to conditions in the isolated gas and represent the two extreme positions of bladder displacement. The vertical distance between the two peaks represents the stroke volume, $V_b$.

To explain the basic response of the wave 21, an equation is used as a model of the circuit. The wave 21 represents the continuous output of the $V_b$ Calculator Circuit 19 or $$V_b = V_d - V_1, \tag{10}$$

where $V_d$ is the continuous compressive displacement $A_p X$ and $V_1$ is the volume lost due to compression of the closed system 146. Substituting $V_1$ as represented by equation (7) into equation (10) and $A_p X$ for $V_d$, $$V_b = A_p X - V_o(1 - P_o/P_m). \tag{11}$$

The equation (11) is an approximation of the circuit of the present invention helpful in understanding the basic response of the present invention.

Beginning with the closed system 146 in a condition of zero compression, the diaphragm position X is equal to zero and the system $P_m$ is equal to $P_o$. Therefore, both terms on the right side of equation (11) are equal to zero and the bladder position represented by $V_b$ is at the zero bladder volume displacement position. As the diaphragm 9 is displaced, both X and $P_{dm}$ rise above zero giving both terms of the equation (11) finite values. While the diaphragm 9 is moving, the pressure in the pump builds up sufficiently to cause blood to start flowing from the bladder. This occurs during the positive slope 23 of the waveform 21. Also during the positive slope 23, the diaphragm 9 reaches its maximum limit when it contacts surface 24 of FIG. 1. The diaphragm 9 is held at this surface for a short period of time before it is released. During this time, blood continues to flow out of the blood pump 1 and the pressure, $P_{dm}$, is decreasing. Accordingly, the $A_p X$ term is constant and the second term of the equation (11) is decreasing so the value of the equation (11) solution is still increasing. When the pressure in cylinder area 13 is released, it releases the pressure in the closed system 146. The pressure in the blood pump drops quickly causing the outlet valve to close as the pressure drops below aortic pressure. The high peak 25 of the wave represents the point at which the diaphragm 9 starts to move back to zero displacement. With the release of pressure in the stroke volume limiter 2, the closed system 146 expands to its atmospheric pressure volume, $V_o$, and the heart starts to fill the bladder 4 with blood causing it to expand. These actions combine to return the diaphragm 9 to its zero displacement position (X=0) during normal pump operation. The diaphragm 9 usually reaches zero displacement before the next compression pulse from the pneumatic driver 3 occurs. With the diaphragm 9 at zero displacement, the wave 21 is again at its low point 22.

This explanation of circuit response covers only the basic operation of the blood pump system. Parameters such as arterial pressure and synchronization with the natural heart vary the response of the circuit output. The Bladder Position Analog signal 27 and the $V_b$ Analog signal 20 of FIG. 1, when connected to chart recorders or other means of visual display, are capable of indicating a wide variety of blood pump conditions allow for very effective monitoring of blood pump operation.

Figure 3:
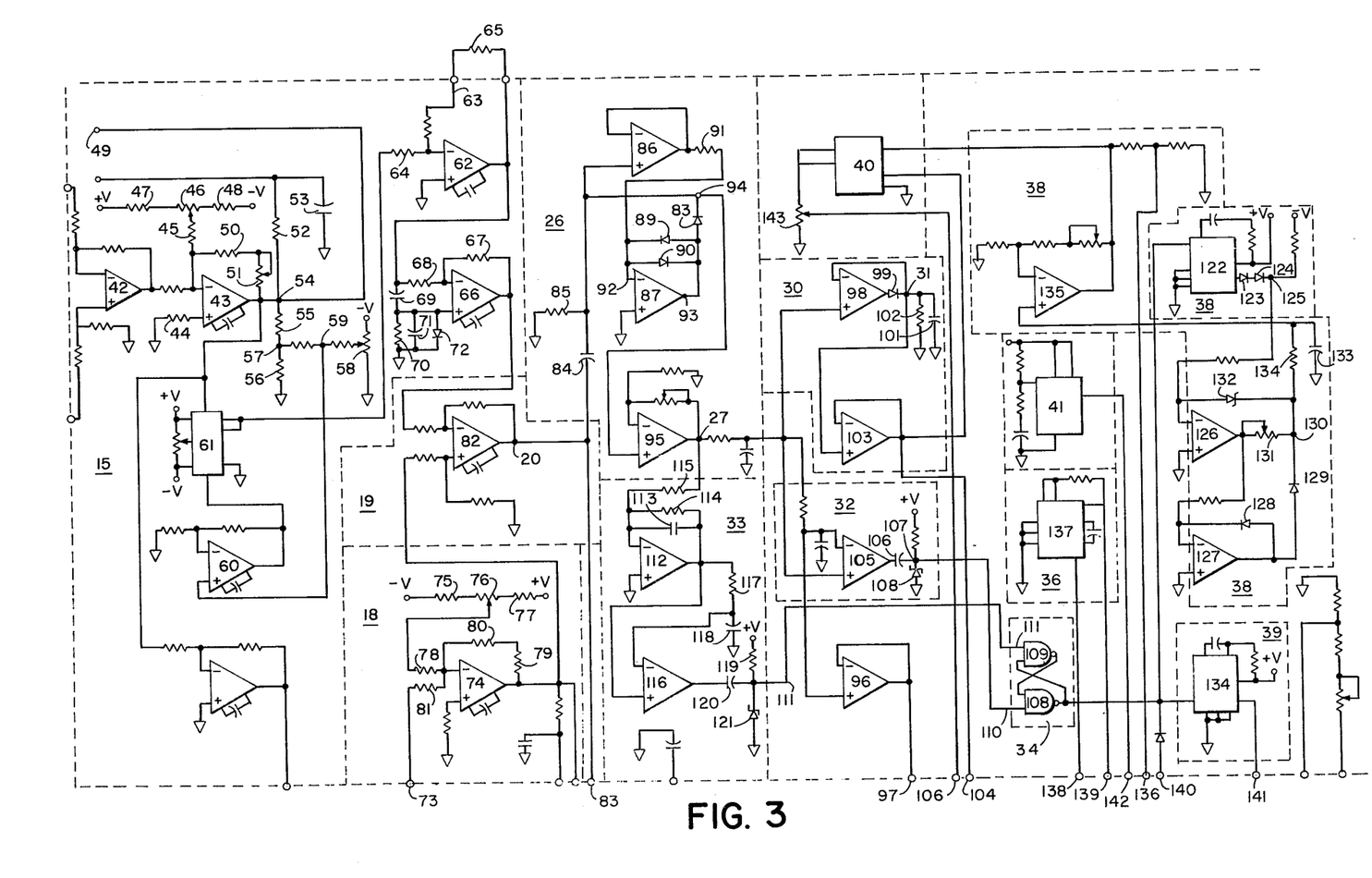
FIG. 3 is a circuit diagram illustrating a preferred embodiment of the invention.

In reference to FIG. 3, functional areas of the circuit which perform functions identifiable with the blocks of FIG. 1 are separated from other areas by dotted lines and numbered as they are in FIG. 1.

The $V_1$ Calculator 15 of FIGS. 1 and 3 determines the volume lost due to compression of the gas in the closed system. The only variable input from the blood pump system required by the calculator 15 is the pressure of the closed pneumatic system 146. This input signal is supplied by an electronic pressure transducer 14. The pressure transducer 14 is a bridge type transducer, the signal being produced across two independent leads. The two independent leads are fed to the positive and negative inputs of summation amplifier 42. The output of amplifier 42 represents the pressure signal as a voltage with respect to ground. This voltage is then fed into the negative input of amplifier 43. The other input of amplifier 43 is connected to ground through a resistor 44. Due to the nature of the pressure transducer 14, it will always provide an output signal even at atmospheric pressures. This in turn will cause an output signal from amplifier 42, even under atmospheric conditions.

To allow an adjustment for varying atmospheric conditions, output signal from amplifier 42 can be cancelled during calibration by resistors 45 through 48, which are also connected to the negative input of the amplifier 43. The output of amplifier 43 is available on a pin 49 of the circuit board. During the calibration procedure the resistor 46 is adjusted until the voltage at pin 49 measures zero.

The negative feedback path of resistors 50 and 51 determines the gain of amplifier 43. The adjustable resistor 51 is used to calibrate this gain. The voltage created at the output of amplifier 43 represents the pressure signal scaled to the level of 24mv/mmHg. A small AC component in this voltage is bled to ground by the resistor 52 and capacitor 53 to permit noise-free calibration of the amplifier 43 to zero volts. The DC voltage at point 54 represents the pressure, $P_t$. The voltage at point 54 is used to calculate $P_t + P_o$, where $P_o$ is a constant and equal to atmospheric pressure. The scaling factor of the signal at point 54 is reduced by the resistors 55 and 56, and the signal appears at point 57. Atmospheric pressure is represented by the voltage at the center tap of the potentiometer 58. The potentiometer 58 is adjusted so that 6.08 volts equals atmospheric pressure (e.g. 760mm Hg). The voltage which appears at the point 59 is the average of the pressure signal and atmospheric pressure. This voltage is fed into the positive input of amplifier 60 and amplified by a factor of 2 so that it now represents the full value, $P_o + P_t$, except for the fact that it has a changed scale. The output of amplifier 60 is fed into an input of the divider 61. The voltage $P_t$ from the output of the amplifier 43 is fed into another input of divider 61. The divider 61 provides an output signal proportional to $P_t/P_o + P_t$. This output is fed into the amplifier 62, the gain factor of which is proportional to the constant value of the volume, $V_o$. Thus, the output of amplifier 62 is from proportional to the direct solution of equation (9), $V_1 = V_o[ P_t/(P_o + P_t)]$. Provision is made to change the gain factor of the amplifier 62 for different values of $V_o$ by changing the resistor 65. The output of amplifier 62 is fed to the negative input of the amplifier 66. The gain of the amplifier 66 is unity, as the values of the feedback resistor 67 and the input resistor 68 are equal. It was found that by selectively reducing the value of $V_1$, as determined by the equation (9), the resulting calculated value of $V_1$ is substantially free of error over the normal blood pump operating ranges. In a preferred embodiment, maximum error is limited to $\pm$ 5%. The correction factor by which this signal is reduced corresponds to a proportion of the rate of change of lost volume due to compression. The amount of signal which is subtracted is determined by the values of a capacitor 69 and a resistor 70. These values are determined empirically by random substitution. The rate of change of the volume is determined by the capacitor 71 which takes the first derivative of the volume signal. The diode 72 only allows this correction factor to be fed to the positive input of amplifier 66 when the loss of volume due to compression is increasing; that is, the correction factor is only used when the pressure in the system is increasing. When the pressure is decreasing, the diode is forward biased and shorts out the correction factor. The output of the amplifier 66 thus represents the loss in volume due to the compressibility of the gas corrected and is to be subtracted from the diaphragm displacement $V_d$ as per equation (10).

The volume displaced by the diaphragm 9, $V_d$, is computed by the $V_d$ Calculator 18 of FIGS. 1 and 3. The input for this circuit is from a linear voltage displacement transducer 16. The transducer used in the circuit is from model number 7308-R2-40 supplied by Pickering and Company of Plainview, New York. The transducer 16 generates a DC signal proportional to the linear displacement of the diaphragm 9. The transducer output is measured with respect to ground and is fed via pin 73 to the negative input of amplifier 74. The zero position of the diaphragm 9 is represented by a voltage zeroed for the amplifier input, as by resistors 75 through 78. The gain of amplifier 74 is determined by resistors 79 through 81. This gain representative of the area of the piston $A_p$, is used to multiply the linear displacement of the piston, X, to achieve displaced volume $V_d$.

The output of amplifier 74 is fed to the positive input of summation amplifier 82. (The amplifier 82 is represented by the $V_b$ Calculator 19 of FIG. 1.) The output of amplifier 66, representing the loss of volume due to compression, is connected to the negative input of amplifier 82 to subtract the loss of volume due to compression $V_1$ from the change of volume due to diaphragm movement $A_p X$.

The output 20 of amplifier 82 is the Bladder Position Analog signal 20'. This signal is available as an output from the circuit at point 83. As previously noted, this signal is generally sinusoidal in shape and its total height represents the stroke volume. The bottom of this signal is set to zero to facilitate measurement of the height and thus the stroke volume. The output signal from the amplifier 82 is fed through capacitor 84 and appears across resistor 85. The two amplifiers 86 and 87, along with diodes 88, 89 and 90, and resistor 91 all function to zero reference the bottom tip of the Bladder Position Analog signal 20'. When this signal is positive with respect to ground, the negative input 92 of the second amplifier is also positive with respect to ground, and the output 93 is negative with respect to ground. This causes diode 90 to be forward biased and the output 93 is held at one diode drop (approximately 0.63 volts) below the input 92. The output 93 is thus maintained at one diode drop below the voltage at point 94. Accordingly, the diode 88 is reverse biased and the bladder position signal is allowed to pass through the zero reference circuit. When the bladder position signal tends to go negative with respect to ground, the negative input 92 also tends to go negative with respect to ground. As a result, the output 93 goes positive and forward biases the diode 89 to hold the output 93 at one drop above zero. This forward biases diode 88 and holds the voltage at point 94 to zero. Thus, the bladder position signal does not force the voltage at point 94 below zero. The amplifier 95 takes the signal and amplifies it slightly to maintain the proper scaling factor. The output 27 of the amplifier 95 is the $V_b$ Analog signal 27'. This signal 27' is passed through the amplifier 96 and is outputed on pin 97. The amplifier 96 has a voltage gain of unity and merely enhances power characteristics of the signal.

As noted in reference to FIG. 1, the $V_b$ Analog signal 27' is connected to the $V_b$ Peak Follower 30. The follower 30 detects the high peak values of each blood pump stroke and stores them. The detecting portion of the follower 30 comprises the amplifier 98 and the diode 99. When the input to the amplifier 98 is positive, so is the output. This positive condition forward biases the diode 99 and the voltage at point 100 follows one diode drop below the input voltage, the voltage gain of the amplifier 98 being equal to 1. The capacitor 101 stores the peak values of the $V_b$ Analog signal 27'. When the input reaches the peak value and starts to decrease in voltage the voltage across capacitor 101 becomes more positive than the amplifier output. This reverse biases the diode 99 so the capacitor 101 can discharge only through the resistor 102. This discharge pattern is incorporated so that the voltage across the capacitor can drop and be responsive to the lower $V_b$ peak values which may occur. The output voltage at point 31 is the $V_b$ Peak Analog signal 31', an analog signal which varies only according to the peak value of the stroke volume. The output signal 31' is passed through amplifier 103, a unity gain amplifier, for better power output capabilities and it is outputed on pin 104.

The $V_b$ Analog signal 27' is also used to generate triggering signals for the A to D converter 29 of FIG. 1. Part of this operation is accomplished by the Negative Slope Detector 32. Both the negative and positive inputs of the amplifier 105 are fed by the $V_b$ Analog signal 27'. However, the capacitor 106 delays the signal to the negative input. As the $V_b$ Analog signal 27' is increasing in value, the delayed input is at a lower positive value than the direct input, causing the output of amplifier 105 to be positive. As the gain of the amplifier 105 is infinity, the output goes to its positive extreme. The capacitor 106 blocks passage of this signal to the point 107. Simultaneously, the zener diode 108 is reverse biased and holds the voltage at point 107 to a positive value determined by the reverse bias voltage of the zener diode 108 and representing a logical "1". As the $V_b$ Analog signal starts to decay, the positive input to amplifier 105 becomes less in value than the negative input. This changes the polarity of the amplifier 105 output and the infinite gain drives the output to its negative maximum. This change drives the voltage at point 107 to a logical zero for a short period to produce a change of state in the Display Trigger Flip-Flop 34.

The Display Trigger Flip-Flop 34 comprises two logic nand gates 108 and 109. The two input lines 110 and 111 are normally both at a logical "1". In the reset condition, gate 108 is at a logical "0" and gate 109 is at a logical "1". The temporary change of line 110 to a logical "0", caused by a response from the Negative Slope Detector 32, causes the output of gate 108 to change to a logical "1", and the output of gate 109 to change to a logical "0". In other words, the response of the Negative Slope Detector 32 to a peak in the $V_b$ Analog signal 27' causes a logical set operation to be performed on the Display Trigger Flip-Flop 34. The reset change of this circuit is caused by similar operation of the Positive Slope Detector 33.

The input to the Positive Slope Detector 33 is the $V_b$ Analog signal 27'. The first function of this circuit is a smoothing of the input signal. This is performed by amplifier 112, capacitor 113 and resistors 114 and 115. The configuration of components 113 and 114 in the feedback circuit is that of an integrator. However, the value of the capacitor 113 is small enough to achieve a smoothing of the wave with a minor delay in the transmission of the wave. The precise timing of the wave is not critical; however, the wave is a normalized sawtooth wave (i.e. sinusoidal in shape). The shape is important to prevent false indications by the Positive Slope Detector 33. Along with the smoothing operation, the amplifier 112 also inverts the $V_b$ Analog signal 27'. The resulting signal is fed to the amplifying circuit represented by components 116 through 121. This amplifying circuit is identical to the Negative Slope Detector 32. However, as it operates on an inverted signal, it detects positive slopes. The electrical operation of the amplifying circuit represented by components 116 through 121 is identical to that of the Negative Slope Detector 32. Its output voltage is normally a positive value which represents a logical "1". Approximate simultaneously with low peak in the $V_b$ Analog signal 27', the output on line 111 goes temporarily to zero volts representing a logical "0". This temporary "0" resets the Display Trigger Flip-Flop 34.

The logical "set" operation of the Display Trigger Flip-Flop 34 is used in calculating the beat rate of the blood pump 1, shown in FIG. 1, and to generate trigger signals for displaying outputs, as described below. The beat rate calculation is performed by components 122 through 134; the resulting signal is in analog form. The set operation of the Flip-Flop 34 triggers the monostable multivibrator 122. The output of this multivibrator is fed through diodes 123 and 124 to point 125. The normal or stable state of the multivibrator output is a logical "1" represented by a positive voltage. The diodes 123 and 124 reduce the positive value this voltage, however a positive value representing a logical "1" is maintained. The astable state of the multivibrator output is a logical "0" represented by zero volts. The astable state is triggered by the "set" operation of the Flip-Flop 34, lasting in the preferred embodiment for 60 milliseconds and changes to the stable state. The diodes 123 and 124 reduce the astable output voltage to a negative value at point 125.

The output of the multivibrator 122 is fed to the negative input of amplifier 126. As the amplifier 126 is used in the infinite gain mode, the output is at the negative voltage limit for the stable state of the multivibrator 122. The output of the amplifier 126 is at the positive voltage limit for the astable state of the multivibrator 122. As the amplifier 126 output is connected to the negative input of the amplifier 127, a stable state for the multivibrator will cause the output of amplifier 127 to go positive in voltage. This forward biases the diode 128 which, in cooperation with the grounded positive input of the amplifier 127, causes the output to be held at one diode drop above ground. When the output of amplifier 126 is at the negative limit, the diode 129 is forward biased. The forward bias voltage drop across the diode 129 causes the voltage at point 130 to approximate zero. The potentiometer 131 adjusts the voltage at point 130 to exactly zero while the multivibrator 122 is in its stable state. The astable state of the multivibrator 122 drives the output of the amplifier 126 to its positive voltage limit, reverse biasing the zener diode 132. The reverse bias voltage of the zener diode 132 precisely controls the voltage at the point 130 during the astable state of the multivibrator 122. The accuracy of the voltage at point 130 during the two multivibrator states and the length of the astable state are used to convert the digital pulses into analog information.

The voltages at point 130 charge and discharge capacitor 133 through resistor 134. During the astable state, the capacitor is being charged by the controlled voltage established by the zener diode 132. During the stable state, the capacitor is being discharged by the zero volts at point 130. More specifically, a square wave 10 volts high and 60 milliseconds long is periodically charging the capacitor. The number of square waves will determine the amount of charge on the capacitor over any given time period. Thus, the amount of charge will represent the number of square waves and, therefore, the number of blood pump beats. In the present circuit, the values of the capacitor 133 and the resistor 134 are chosen so that the charge and discharge rates are essential linear over the time periods needed between pulses of the blood pump system. This makes the charge on the capacitor linearly proportional to the number of blood pump beats. The average charge on the capacitor is read as the median voltage between the maximum charge condition and the minimum charge condition. This is achieved by outputting, to the A to D Converter 29 of FIG. 1, the voltage across capacitor 133, after it has been properly scaled, and generating a trigger signal for it exactly halfway through the astable state of the multivibrator 122. The trigger signal is generated by the monostable multivibrator 134. The multivibrator 134 has an astable state of 30 milliseconds or one-half that of the multivibrator 122. This multivibrator 134 corresponds to the B.P.M. Trigger 39 of FIG. 1.

The scaling of the analog beat rate signal across capacitor 133 is adjusted by the amplifier 135 and its connected circuitry. The output which goes to the Output Selector Switch 28 appears on pin 136. This output is also used to calculate the flow rate.

Although it is scaled differently, the beat rate signal is connected to one of the inputs of the flow rate Multiplier 40. The other input to Multiplier 40 is the $V_b$ Peak Analog signal 31'. The resulting output is scaled by potentiometer 143 and is available on pin 106. This signal represents the flow rate produced by the blood pump 1. The sampling of this signal by the A to D Converter 29 (shown only in FIG. 1) is triggered by a signal from a Five (5) Second Pulse generator 41.

As mentioned in reference to FIG. 1, each of the analog outputs is fed into the A to D Converter 29 by selection of the Switch 28, the Display Trigger 36 signaling the A to D Converter 29 of FIG. 1 when to sample the analog signal. This signal comprises a single square wave pulse of a duration required by the design of the A to D Converter 29 being used. The display trigger pulse for the present invention is generated by the monostable multivibrator 137. This multivibrator is triggered by an input on pin 138 and the output, on pin 139, is connected to the A to D Converter 29 of FIG. 1.

Figure 4:
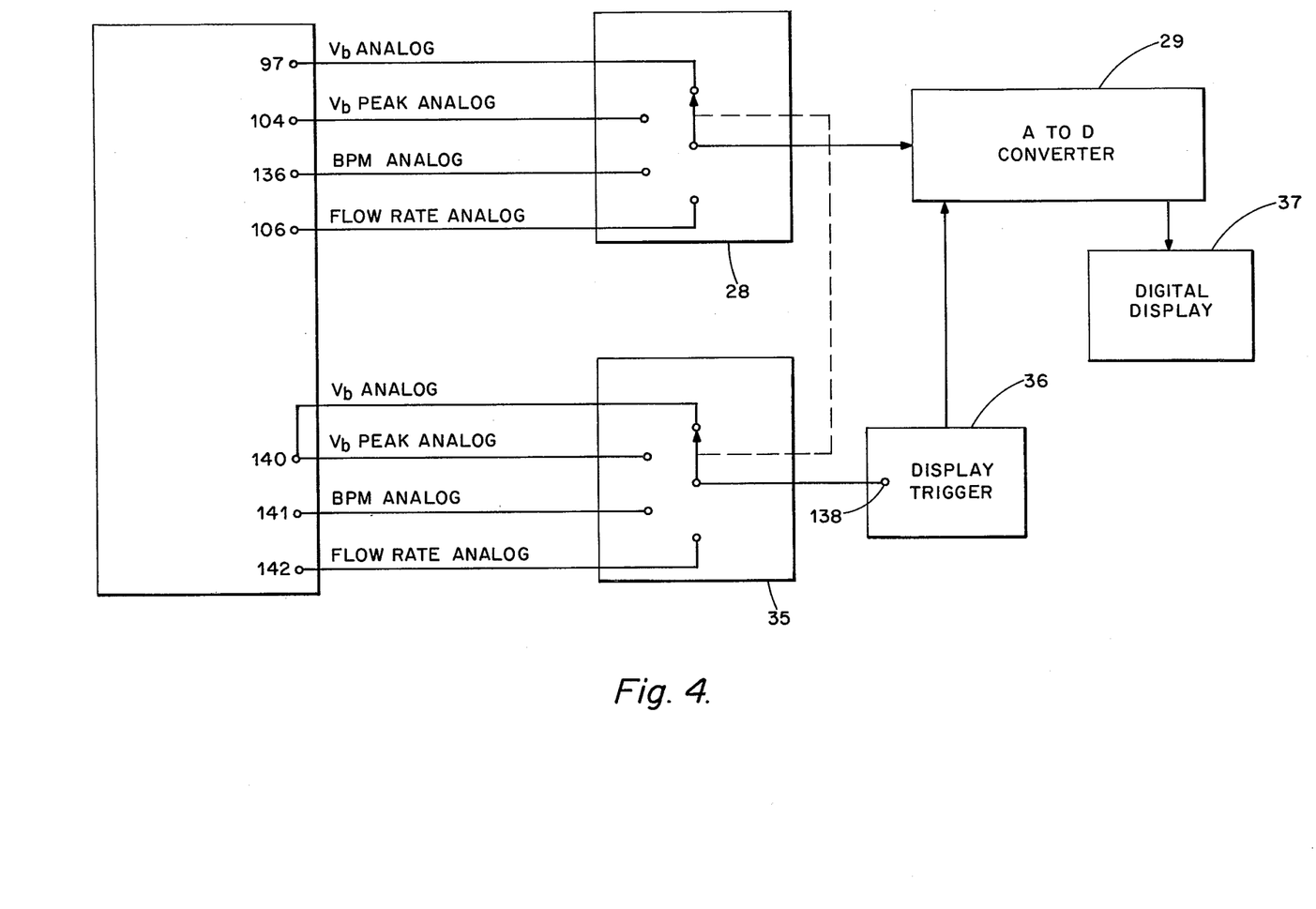
FIG. 4 is a circuit diagram of the switches 28 and 35 shown in FIG. 1.

The Output Selector Switch 28, shown in FIG. 4, selectively connects the following output pins for the respective output signals to the A to D Converter: pin 97, $V_b$ Analog 27; pin 104, $V_b$ Peak Analog 30; pin 136, Beats Per Minute Analog; pin 106, Flow Rate Analog.

The Trigger Select Switch 35, shown in FIG. 4, which is ganged to the Output Selector Switch 28 connects the appropriate trigger signal to the input pin 138 of the Display Trigger 36. The appropriate trigger signals for the various output signals appears on the following pins: $V_b$ Analog 27, pin 140; $V_b$ Peak Analog, pin 140; Beats Per Minute Analog, pin 141; Flow Rate Analog, pin 142.

I claim:

1. A device for monitoring the operation of a blood pump, said blood pump having a flexible bladder enclosed by a rigid housing and confining therebetween a closed system of gas, said closed system being adapted to undergo repetitive pressurizations resulting from known and repetitive volumetric compressive displacements for repeatedly volumetrically collapsing said bladder, said monitoring device comprising:
    means for receiving a first signal, said first signal being variable as a function of the pressure internal of said closed system;
    analog electronic means responsive to said first signal from said first receiving means for substantially continuously generating a second signal functionally related to the loss of volume of said closed system produced by each said repetitive pressurization;
    means for generating a third signal varying as a function of said known volumetric compressive displacement; and
    second analog electronic means for subtracting said second signal from said third signal for substantially continuously generating a fourth signal functionally related to the volumetric position of said bladder.

2. The device of claim 1, further comprising:
    third electronic means responsive to said fourth signal for generating a fifth signal functionally related to the time of the maximum amount of said bladder collapse; and
    analog fourth electronic means responsive to said fifth signal and said fourth signal, for generating a sixth signal functionally related to the maximum amount of bladder collapse for each of said repetitive injections, and for converting said sixth signal into digital form.

3. The device of claim 1, further comprising analog fifth electronic means responsive to said fourth signal for generating a seventh signal functionally related to the maximum amount of bladder collapse for each of said repetitive injection, and for storing said seventh signal, until the next sequential seventh signal is determined.

4. The device of claim 3, further comprising sixth electronic means for converting said stored seventh signal into digital form.

5. The device of claim 3, further comprising: third electronic means responsive to said fourth signal for generating a fifth signal functionally related to the time of the maximum amount of said bladder collapse;
    seventh electronic means responsive to said fifth signal for generating an eighth signal functionally related to the repetition rate of said blood pump; and analog eighth electronic means for multiplying said fifth signal by said eighth signal for generating a ninth signal functionally related to the rate of bladder collapse.

6. The device of claim 5 further comprising
ninth electronic means responsive to said fifth signal for converting said ninth signal into digital form.

7. The device of claim 1, further comprising:
third electronic means responsive to said fourth signal for generating a fifth signal functionally related to the time of the maximum amount of bladder collapse;
seventh electronic means responsive to said fifth signal for generating an eighth signal functionally related to the repetition rate of said blood pump; and
tenth electronic means responsive to said fifth signal and said eighth signal for generating a tenth signal functionally related to the repetition rate of said blood pump.

8. An electronic device for computing the volume lost by a closed system confining a fixed quantity of gas undergoing a continuously measured pressurization caused by a known compressive displacement, comprising:
first analog electronic means for computing a value for the relationship $V_o(P_m - P_o/P_m)$ wherein $V_o$ is the volume of said fixed quantity of gas absent said known displacement, $P_o$ is the pressure of said closed system absent said known displacement and $P_m$ is said pressurization measurement;
second analog electronic means, using first said value, for determining a second value, proportional to the rate of change of the first said value and for determining whether said first value is increasing or decreasing; and
third analog electronic subtraction means, responsive to said first and second electronic means, for reducing first said value by said second value during such portions of first said value where first said value is increasing.

9. An electronic device for computing the volume lost by a closed system confining a fixed quantity of gas undergoing a continuously measured increased pressure caused by a known compressive displacement, comprising:
first analog electronic means for computing a value for the relationship $V_o(P_t/P_o + P_t)$ wherein $V_o$ is the volume of said fixed quantity of said closed system absent said known displacement, $P_o$ is the pressure of said closed system absent said known displacement and $P_t$ is said pressure increase;
second analog electronic means, using first said value, for determining a second value, proportional to the rate of change of first said value and for determining whether first said value is increasing or decreasing; and
third analog electronic subtraction means, responsive to said first and second electronic means, for reducing first said value by said second value during such portions of first said value where first said value is increasing.

10. Apparatus for monitoring the operation of a blood pump which includes a flexible bladder normally capable of expansion for the intake of blood and collapse for the ejection of blood in the presence of pressure external thereto comprising:
a closed pneumatic system of known volume enclosing said bladder;
a fixed quantity of compressible gas contained in said closed system;
means for periodically reducing said known volume of said closed system to apply external pressure to collapse said bladder and for returning said closed system to said known volume to remove external pressure from said bladder;
transducing means connected to said closed system for generating a first signal varying continuously with the pressure of said compressible gas in said closed system;
electronic means keyed to said known volume of said closed system and responsive to said first signal for generating a second signal functionally related to volumetric changes in said closed system caused by compression of said gas;
means connected to said closed system for generating a third signal varying continuously as a function of the position of said means for periodically reducing said known volume of said closed system; and
electronic means for continuously subtracting said second signal from said third signal for continuously generating a fourth signal functionally related to the volumetric configuration of said bladder.

* * * * *